United States Patent [19]

Weiss et al.

[11] 4,041,947
[45] Aug. 16, 1977

[54] FLOW CONTROL SYSTEM

[75] Inventors: Steven N. Weiss, New York; Alan Broadwin, Brooklyn, both of N.Y.

[73] Assignee: Cavitron Corporation, New York, N.Y.

[21] Appl. No.: 589,484

[22] Filed: June 23, 1975

Related U.S. Application Data

[62] Division of Ser. No. 437,165, Jan. 28, 1974, Pat. No. 3,902,495.

[51] Int. Cl.² .................. A61M 1/00; G05D 11/11
[52] U.S. Cl. ............................ 128/276; 137/115
[58] Field of Search .................. 128/276; 137/115

[56] References Cited

U.S. PATENT DOCUMENTS

| 2,395,941 | 3/1946 | Rockwell | 137/115 X |
| 2,665,704 | 1/1954 | Kanuch | 137/115 X |
| 3,589,363 | 6/1971 | Banko et al. | 128/276 |
| 3,815,604 | 6/1974 | O'Malley et al. | 128/276 X |
| 3,902,495 | 9/1975 | Weiss et al. | 128/276 |

*Primary Examiner*—Channing L. Pace
*Attorney, Agent, or Firm*—Philip Sperber; Kenneth Olsen

[57] ABSTRACT

A fluidic control system for use in irrigation and aspiration of the anterior chamber of the eye during ultrasonic emulsification of a cataract therein. The system comprises a handpiece with an (ultrasonically vibrated) hollow tip, the hollow tip being connected to the fluid withdrawal or aspirating portion, while an annular passage around the tip is used to introduce fluid for irrigation purposes. The aspirating portion comprises a withdrawal hose attached to the output manifold of the handpiece in fluid communication with the hollow tip, a constant flow pump attached to the other end of the withdrawal hose, and a vacuum relief valve connected to the withdrawal hose intermediate the pump and the handpiece. The irrigation portion comprises a fluid supply bottle at a predetermined height above the eye, and administration set attached to the bottle, and an inflow hose attached to the intake manifold of the handpiece and in fluid communication with the annular passage. All the aforementioned components are in fluid communication with the anterior chamber of the eye during removal of a cataract by insertion of the handpiece tip into the eye chamber.

5 Claims, 2 Drawing Figures

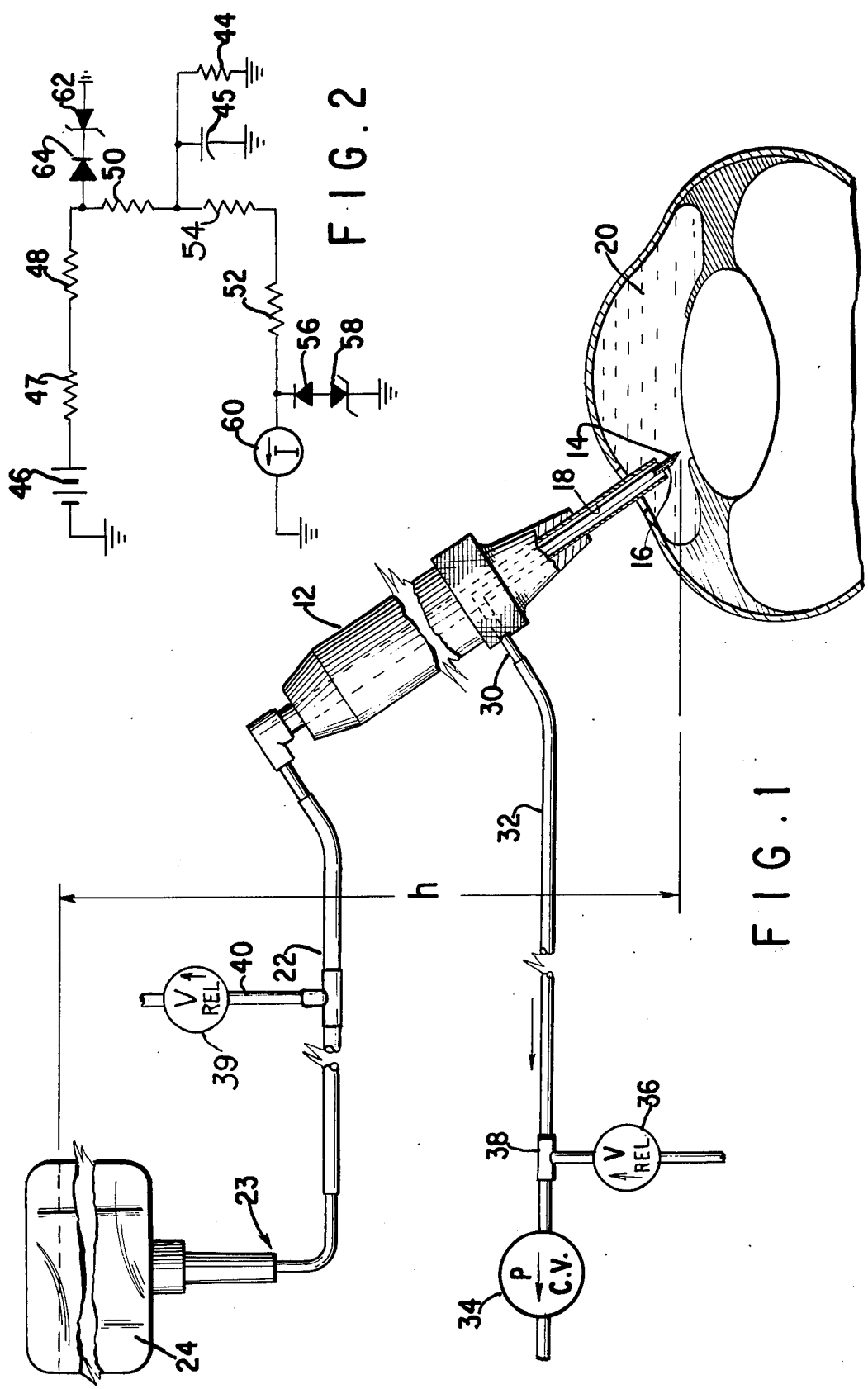

FLOW CONTROL SYSTEM

This is a division, of application Ser. No. 437,165, filed Jan. 28, 1974 now U.S. Pat. No. 3,902,495 issued Sept. 2, 1975.

BACKGROUND OF THE INVENTION

This application relates to an improvement in the control of fluid flow in a surgical device. More particularly this invention relates to an improvement in the fluid flow systems for a surgical device useful in cataract removal such as that shown by U.S. Pat. No. 3,589,363 issued June 29, 1971 to A. Banko and C. D. Kelman for a Material Removal Apparatus and Method Employing High Frequency Vibrations. The aforesaid patent describes an instrument for breaking apart and removing unwanted tissue and material especially a cataract located in the anterior chamber of the eye by ultrasonically fragmenting the cataract while simultaneously introducing fluid into the eye chamber, and withdrawing the fluid and fragmented cataract particles. Briefly the device described includes a handpiece having an operative tip vibrating in the ultrasonic range which is also hollow and is in turn surrounded by a tubular sleeve. In operation the tip of the handpiece including the surrounding tubular sleeve are inserted into the anterior chamber of the eye. Treatment fluid is introduced through the hollow sleeve at a constant low pressure. This introduction of fluid which is called irrigation is to provide a replacement for fluid withdrawn or lost from the eye chamber. The withdrawl of fluid and suspended material from the anterior chamber is specifically called aspiration and ideally there is no change in fluid content or anterior chamber pressure as a result of irrigation-aspiration. This of course is impossible to achieve since aspiration is intended to remove solids which until broken up sometimes tend to occlude or block the fluid withdrawl openings of the handpiece.

This problem with control of fluid content and pressure within the anterior chamber of the eye during irrigation-aspiration is discussed in detail in U.S. Pat. No. 3,693,613 issued Sept. 26, 1972 to Charles Kelman for a Surgical Handpiece and Flow Control System for Use Therewith, and commonly assigned herewith.

A handpiece described in the aforesaid U.S. patent. as well as the instrumentation described in U.S. Pat. No. 3,589,363 provides a tool tip insertable in the anterior chamber of the eye with an annular nozzle for supply of fluid for irrigation, a hollow tool tip which is vibrated at about 40,000 cps to provide the energy to break up the cataract and allow fluid withdrawl for aspirating the reduced particles and fluid. When the handpiece is inserted into the eye, it is extremely important to maintain the fluid pressure of the chamber within a certain range and to prevent rapid fluctuations of the pressure and fluid content of the chamber. A collapse of the anterior chamber for lack of sufficient pressure could result in damage to soft tissues of the eye as well as possible damage of the eye posterior capsule itself from contact of the tissues with the vibrating tool tip. This problem of maintaining the proper pressure is a particularly difficult and sensitive one and is one of the problems which the apparatus shown in the aforesaid U.S. Pat. No. 3,693,613 was designed to solve. The system shown therein while satisfactory is quite obviously a rather complex apparatus which requires in terms of control, close and competent operation personnel. Thus as part of the operation to remove a cataract from the anterior chamber of the eye the handpiece is inserted into the chamber through a small incision and the fluid flow adjusted to the desired level principally by the height at which the irrigation fluid source is supported to provide a gravity flow into the eye, and the speed of a constant flow positive displacement pump in the piping from the eye to withdraw the aspirating stream. The surgeon then moves the cataract lens into the anterior chamber, applies the ultrasonic vibration to the tip of the handpiece in contact with the lens and proceeds to break up the lens.

As part of the application of the tip to the lens the opening in the tip through which aspiration proceeds is periodically occluded by lens material. During such occlusion, fluid is prevented from entering the hollow tip, although the constant flow pump continues to operate. The pump operation thus starts drawing a vacuum in the conduit between the handpiece tip and the pump. At the same time, the pressure from the gravity feed of irrigation fluid into the eye remains constant and increases fluid pressure in the anterior chamber of the eye, expanding it somewhat. However once the opening into the handpiece tip is uncapped by fragmentation of the occlusion, the high vacuum existing in the aspirating system tends to quickly withdraw fluid from the anterior chamber. This may rapidly decompress the anterior chamber and draw the enclosing tissues towards the handpiece tip. Besides the danger represented by the ultrasonic vibrations of the handpiece tip on contact with these tissues, the rapid decompression itself may be injurious to the tissues. The apparatus shown by the aforesaid U.S. Pat. No. 3,693,613 of course is designed to eliminate such pertubrations to the eye by monitoring and controlling flow. It would be advantageous to have a system which is not only fail-safe by means of being simple rather than complex, but is also more easily regulated and controlled by normal operative personnel rather than trained technicians.

SUMMARY OF THE INVENTION

Accordingly we have invented a fluidic flow system for use in the irrigation and aspiration of a small elastic pressure responsive chamber. The system comprises: a fluid source under substantially constant pressure; fluid inflow means connected to the fluid source for limiting flow of the fluid from the source into the chamber thereby providing irrigation fluid at a predetermined limited flow rate and pressure into the chamber; fluid withdrawal means in fluid communication with the chamber for aspirating fluid from the chamber at a rate to eliminate transient pressure shocks to the chamber; a constant flow pump connected to the other end of the fluid withdrawl means, with the pump acting to draw fluid from the chamber through the withdrawal means; and the withdrawal means including a pressure differential relief valve intermediate the chamber and the pump, the relief valve responsively opening at a predetermined pressure differential which in combination with the parameters of the fluid withdrawal means limits the occurrence of pressure transients communicated to the chamber, whereby flow resistivity of the withdrawal means between the chamber and the valve attenuates the pressure changes transmitted to the chamber when the valve opens in response to the predetermined pressure differential between atmosphere and the pressure in the withdrawal means reaching the predetermined differential pressure. Preferably where the enclosed volume is the anterior chamber of the eye, the relief valve opens to atmosphere in response to a pressure differential of from 10 mm of mercury (Hg) to 100 mm Hg; the pressure of the fluid source is in the range of from 10 to 100 mm Hg; the flow resistivity of the inflow means is from 0.042 to 18.5 mm Hg per ml per min; the flow resistivity of the fluid withdrawal means is from 0.35 to 21.5 mm Hg ml per min; and the constant flow volume of the pump is from 5 to 50 ml per min. More particularly the preferred pressure, flow and flow resistivity ranges of the system according to the present invention comprise the following: a fluid source exerting a constant pressure of from 30 to 60 mm Hg; the inflow means having a flow resistivity of from 0.5 to 2.5 mm Hg. ml per min between the fluid source at one end and to the operative volume of the anterior chamber of an eye at the other end; the fluid withdrawal means having a flow resistivity of from 1.33 to 3.0 mm Hg. per ml per min. from the operative volume of the anterior chamber of the eye and to the atmosphere; the constant volume pump having a flow rate of from 20 to 30 ml per min; and the relief valve connected to the flow withdrawal means intermediate the pump and the eye chamber responsively opening the atmosphere at a pressure differential of between about 30 and 50 mm Hg.

It is therefore an object of this invention to provide a fluidic control system for use in irrigating and aspirating a small enclosed elastic volumetric space.

Another object of the present invention is to provide an effective flow control system for irrigating and aspirating the anterior chamber of the eye.

Yet another object of the present invention is to provide a flow control system for effectively limiting the transient pressure and flow changes as felt by the anterior chamber of the eye during irrigation and aspiration thereof.

Other objects and advantages of the system according to the present invention will be apparent from the brief description of the drawings and the preferred embodiment which follows.

BRIEF DESCRIPTION OF THE DRAWINGS

FIG. 1 of the drawings is a diagram of the fluidic flow control system of the present invention; and FIG. 2 of the drawings is an electrical circuit analog of the flow control system of FIG. 1.

DESCRIPTION OF THE PREFERRED EMBODIMENT

In the U.S. Pat. No. 3,589,363 described hereinbefore and which is incorporated herein by reference, apparatus and method for the removal of material by employing high frequency vibration is shown and described. Briefly the aforesaid patent describes an instrument for breaking apart and removing unwanted material such as for surgically removing a cataract from the eye. The apparatus includes a handpiece having an operative tip vibrating at a frequency in the ultrasonic range (preferably about 40,000 cps) with an amplitude controllable up to several thousandths of an inch. The operative tip is itself hollow and is in turn surrounded by a tubular sleeve forming an annular passage. The inflow fluid for irrigating the anterior chamber of the eye is introduced into the chamber through the annular passage and the broken up material, small particles and fluid in the eye, is withdrawn at the same time through the hollow tip to aspirate the chamber.

Referring now to FIG. 1 of the drawings wherein a simplified diagram of a handpiece 12 is shown with an operative tip 14 having a hollow withdrawal means 16, and an annular passage 18 surrounding the tip 14 for introducing fluid into an anterior chamber 20 of an eye undergoing cataract surgery. For a more detailed description of the handpiece 12 described above, reference is made to the handpieces shown in the aforesaid U.S. Pat. Nos. 3,589,363 and 3,693,613 commonly assigned to the assignee herein.

Irrigation fluid is introduced into the handpiece 12 via an inflow hose 22 which is connected at one end to the handpiece and at the other end to an administration set 23, that is a hose connected to an irrigation fluid supply bottle 24 suspended by an appropriate bracket (not shown) a fixed height $h$ over the level of the handpiece and eye. The fixed height $h$ at which the fluid supply bottle is suspended acts to apply a fixed fluid pressure to fluid entering the hose 22 from the bottle to the eye. The selected height is such as to apply a pressure of from about 10 mm Hg to about 100 mm Hg to fluid entering the administration set and thereby furnish a fluid source having a constant preselected pressure level in relation to the handpiece.

More preferably the height at which the supply bottle is suspended is such as to apply a pressure head of from 30 mm Hg to 60 mm Hg. According to the present invention, this is the sole means for supplying the pressure head which forces the flow of fluid from the bottle through the administration set 23, the inflow hose 22 and the annular passage of the handpiece into the anterior chamber of the eye.

For purposes of this invention the pressure which is internally applied to the eye is of prime importance. For instance, as described in U.S. Pat. No. 3,693,613, it is very important that pressure of the anterior chamber of the eye be maintained within a certain range of values to prevent damage thereto. A collapse of the anterior chamber due to reduced pressure could result in either the iris, the endothelium layer of the cornea, or the posterior capsule as well as other soft tissue, coming in contact with the operating tip of the handpiece. This problem of maintaining the proper pressure is a particularly difficult and sensitive one in the case of an operative site such as the anterior chamber, which is considerably small in volume than the volume of fluid necessary for continuous irrigation and aspiration. The anterior chamber of the eye is of course, in the same pressure related system as the apparatus of this invention. In a cataract operation, pressure transients are periodically being induced at the tip of the handpiece due to the presence of a particle or part of the cataract. This initially prevents entry of aspirating fluid into the tip with resulting buildup of suction in the tip, and then sudden clearance of the occlusion blocking the handpiece tip. The apparatus shown in the U.S. Pat. No. 3,693,613 is designed to reduce and overcome this problem and as such is effective though expensive and complicated.

Basically the present invention provides an irrigation system which limits the fluid pressure to which the anterior chamber of the eye is subject by limiting the height at which the irrigation fluid supply is maintained in reference to the eye, and by further limiting the flow rate into the eye utilizing specified inflow means having a specified resistivity to flow, as well as relating the irrigation system to the fluid withdrawal or aspiration system. That portion of the fluidic system comprising the fluid withdrawl means, the constant flow pump and the differential pressure relief valve act in combination to limit fluid flow from the eye, and more importantly prevent sudden pressure changes or pressure transients from occuring by increasing the time period over which the pressure changes occur and by limiting the maximum pressure drop to which the eye would be exposed. This is accomplished by controlling the constant flow rate of the pump; by setting a predetermined limit to the pressure differential, the relief valve will open to atmosphere; and by controlling the flow resistivity of the fluid piping as herein described.

Referring back to FIG. 1 of the drawing the operative tip 14 of the handpiece is hollow and has an internal fluid withdrawal passage 30 constituting part of the fluid withdrawal system of the present invention utilized in aspirating the operative site of the eye. A fluid withdrawal pipe 32 is connected to the handpiece at one end and is in fluid communication with the fluid withdrawal passage. The other end of the fluid withdrawal pipe is connected to a constant flow pump 34 preferably a constant displacement, variable speed, peristaltic pump. The peristaltic feature acts to avoid any contact of the operating parts with the withdrawn fluid suspension. Intermediate the pump 34 and the handpiece, a relief valve 36 is connected by a T joint 38 to the fluid withdrawal pipe and is set to open to atmosphere should the pressure differential in the fluid withdrawal pipe exceed a predetermined pressure, which pressure may be from 30 mm Hg to 50 mm Hg. Preferably the pressure differential at which the relief valve opens is a pressure of about 40 mm Hg. Constant flow capacity of the pump is preferably a flow of from about 20 ml per min to 30 ml per minute. Flow resistivity of the fluid withdrawal means at these preferred conditions is from about 1.33 mm Hg to about 3.0 mm Hg. Flow resistivity in the fluid inflow system is on the order of from about 0.5 to about 2.5 mm Hg per ml per min.

We have therefore described an effective, economical system for irrigating and aspirating the anterior chamber of the eye during an operation involving the insertion of a handpiece through a small incision in the eye and during which parts of the eye such as a cataract are reduced by the action of an ultrasonically vibrating tip. With reference to further understanding the operation of our invention reference is now made to FIG. 2 of the drawing which shows the electrical analog circuit which led to the fluidic control system of this invention. It must be further understood that each part of our invention functions in relation to a moderately uncontrollable set of conditions imposed by the needs of the operative site, i.e., anterior chamber of human eye and the size of the operative incision. The conditions in the anterior chamber of the eye are analogized by two electrical elements which are a resistive element 44 to account for flow resistivity through the incision, and a capacitor 45 to correspond to elasticity of the eye chamber, both elements being in parallel and connected to ground at one end and at the other end to the inflow irrigation system and the fluid withdrawal system. The fluid inflow system is analogized by a constant voltage source 46 corresponding to the fluid supply bottle set at a specified height to provide a constant pressure head; administration set resistance 47 corresponding to the flow resistivity thereof; an inflow resistance 48 corresponding to flow resistivity of the inflow hosing, and a resistance 50 corresponding to the flow resistivity of the fluid inflow manifold of the handpiece. For the withdrawal system a pipe resistance 52 corresponds to the resistivity imposed in the fluid withdrawal piping, and of the handpiece by outflow manifold resistance 54.

The relief valve is analogized by a diode 56 and a zener diode 58 back to back in series at one end to the fluid withdrawal pipe and at the other end to ground (or atmosphere). The constant flow pump is analogized by inserting a hypothetical electrical current element 60 acting as a constant current source. In terms of the electrical analogues of the fluidic parameters, resistance (R) is equivalent to flow resistance in pressure terms; voltage (V) is equivalent to a pressure source in mm Hg; and current amperes (I) is equivalent to flow in ml per min. Utilizing the above analogy we have been able to conceive and build our invention and relate various known conditions in determining the operative parameters which are described hereinbefore.

The system is able to accomplish the irrigation-aspiration of the anterior chamber of the eye, while at the same time reducing transients introduced by occlusions of the fluid withdrawal or aspirating system. It can be seen that by our invention, we have provided a simplified though quite effective fluidic control system for use in conjunction with the operative system described herein and in the aforesaid U.S. Pat. No. 3,589,363 and which provides the safeguards, effectiveness, ease of use, and operative usefullness desired by the system shown in U.S. Pat. No. 3,696,613.

Our invention may be employed with certain modifications and variations. For instance, the irrigation portion of our system may be employed without the aspiration system. In this mode of employment flow of fluid into the eye is as previously described while flow of fluid out of the anterior chamber of the eye is through the opening or incision made therein for the insertion of the handpiece tip. A modification of the irrigation system is shown in the drawings in solid line, where a pressure means for relief of undue pressure head is employed. The pressure means comprises a pressure relief valve 39 connected to the inflow hose 22 by a tube 40. The pressure relief valve 39 is selected to prevent undue pressure from being applied through the irrigation system to the eye chamber. The analogous components shown in FIG. 2 of the drawings to such a pressure relief means incorporated in the irrigation system comprise a diode 64 connected to the circuit between resistors 48 and 50 and a zener diode 62 connected back to back with the diode 64. The zener diode anode is connected to ground (atmosphere). By this variation we are able to further limit the pressure which can be communicated to the eye chamber through the irrigation system.

Having thus described our preferred embodiment and wishing to cover those aspects of our invention which would be apparent to those skilled in the art, from the invention herein but without departing from either the spirit or scope thereof.

We claim:

1. A fluidic flow system for use in irrigation of a small elastic pressure responsive chamber, said chamber having an opening therein for fluid communication with said chamber, said flow system comprising an irrigation fluid source at a preselected pressure of from about 10 to 100 mm Hg, fluid inflow means connected to said fluid source and suitable for fluid communication with said chamber through said opening, said fluid inflow means having a flow resistivity of from about 0.42 to 18.5 mm Hg per ml fluid per min so that the flow of the fluid from said source into said chamber is limited to a maximum predetermined flow rate, and pressure limiting means in fluid communication with said fluid inflow means intermediate said chamber and said fluid source, said pressure limiting means operative in response to a predetermined pressure of being about 10 and 100 mm Hg in said fluid inflow means to limit in cooperation with said flow resistivity the pressure of the fluid intended for inflow to said chamber to said predetermined pressure.

2. The fluidic flow system of claim 1 wherein said pressure means is a valve for limiting the pressure of fluid from said source to said chamber.

3. A method of providing irrigation to a small elastic pressure responsive chamber, said method comprising the step of: supplying fluid to a fluid inflow means at a pressure of from about 10 to 100 mm Hg; controlling the flow rate of said fluid through said inflow means by applying a flow resistivity of from about 0.42 to 18.5 mm Hg per ml fluid per minute; limiting the pressure of said controlled fluid to a predetermined pressure of between about 10 and 100 mm Hg, and introducing said controlled, pressure-limited fluid into the chamber.

4. The fluidic flow system according to claim 1 wherein said fluid source pressure is in the range of from about 30 to 60 mm Hg, said fluid inflow means has a flow resistivity of from about 0.5 to 2.5 mm Hg, per ml per min. and said pressure limiting means is operative at a differential pressure between about 30 and 50 mm Hg.

5. The fluidic flow system of claim 1 wherein the chamber is the anterior chamber of an eye and the opening is an incision therein.

* * * * *